(12) United States Patent
Rajfer et al.

(10) Patent No.: US 10,406,196 B2
(45) Date of Patent: Sep. 10, 2019

(54) COMPOSITIONS AND METHODS FOR TREATING, INHIBITING THE ONSET, AND SLOWING THE PROGRESSION OF ERECTILE DYSFUNCTION INCLUDING NATURALLY OCCURRING AGE RELATED ERECTILE DYSFUNCTION

(71) Applicant: K.L.R.M., LLC, Long Beach, CA (US)

(72) Inventors: Jacob Rajfer, San Pedro, CA (US); Mauro Milchteim, Chapel Hill, NC (US); Floyd Alexander Katske, Los Angeles, CA (US)

(73) Assignee: K.L.R.M., LLC, San Pedro, CA (US)

( * ) Notice: Subject to any disclaimer, the term of this patent is extended or adjusted under 35 U.S.C. 154(b) by 689 days.

(21) Appl. No.: 13/786,117

(22) Filed: Mar. 5, 2013

(65) Prior Publication Data
US 2014/0255528 A1 Sep. 11, 2014

Related U.S. Application Data

(63) Continuation-in-part of application No. PCT/US2011/056965, filed on Oct. 16, 2011, which is a continuation of application No. 12/907,113, filed on Oct. 19, 2010, now abandoned.

(51) Int. Cl.
| A61K 36/9068 | (2006.01) |
| A61K 31/198 | (2006.01) |
| A61K 36/63 | (2006.01) |
| A61K 36/77 | (2006.01) |

(52) U.S. Cl.
CPC ........ *A61K 36/9068* (2013.01); *A61K 31/198* (2013.01); *A61K 36/63* (2013.01); *A61K 36/77* (2013.01)

(58) Field of Classification Search
None
See application file for complete search history.

(56) References Cited

U.S. PATENT DOCUMENTS

| 5,594,032 | A | 1/1997 | Gonzalez-Cadavid et al. |
| 6,007,824 | A | 12/1999 | Duckett et al. |
| 6,133,281 | A | 10/2000 | Gonzalez-Cadavid et al. |
| 6,866,872 | B1 | 3/2005 | Tomi et al. |
| 2002/0051826 | A1 | 5/2002 | Darland et al. |
| 2003/0130183 | A1 | 7/2003 | Southard et al. |
| 2004/0265400 | A1 | 12/2004 | Barone et al. |
| 2005/0085486 | A1 | 4/2005 | Gonzalez-Cadavid et al. |
| 2009/0274722 | A1 | 5/2009 | Ligums |
| 2009/0150421 | A1 | 6/2009 | Rjaibi et al. |
| 2010/0129467 | A9 | 5/2010 | Albritton |
| 2012/0121740 | A1 | 5/2012 | Rajfer |

FOREIGN PATENT DOCUMENTS

| CA | 2702045 A1 | 4/2009 |
| CN | 101642226 A | 2/2010 |
| CN | 101820871 A | 9/2010 |
| CN | 201180060449.1 | 8/2014 |
| CN | 201180060449.1 | 7/2015 |
| CN | 201180060449.1 | 2/2016 |
| EP | 2210600 A1 | 7/2010 |
| EP | 11841157.8 | 3/2014 |
| EP | 263705 B1 | 8/2015 |
| JP | 09157163 | 6/1997 |
| JP | 2000316528 A | 11/2000 |
| JP | 2002193826 | 7/2002 |
| JP | 2010195761 A | 9/2010 |
| TW | 100137976 | 7/2015 |
| WO | WO0035466 A1 | 6/2000 |
| WO | WO0067768 A1 | 11/2000 |
| WO | WO2008105384 A1 | 9/2008 |
| WO | WO2009121687 A1 | 10/2009 |
| WO | WO2009150421 A2 | 12/2009 |
| WO | PCT/US2011/056965 | 3/2012 |
| ZA | 995697 A | 1/2000 |

OTHER PUBLICATIONS

Drewes (Phytochemistry (2003), vol. 62, pp. 1019-1025).*
Schwartz, Eric, et al., "Slidenafil Preserves Intracorpeal Smooth Muscle After Radical Retropubic Prostatectomy," The Journal of Urology, vol. 171, pp. 771-774, Feb. 2004.
Dorsey, Philip et al., "Phosphodiesterase type 5 (PDE5) inhibitors for the treatment of erectile dysfunction," Expert Opinion, Pharmacother. (2010), 11(7): pp. 1109-1122.
Imanishi, Nobuko et al., "Inducible Activity of Ginger Rhizome (Zinguber Offifinale Rosc.) on the mRNA Expression of Macrophage-Inducible Nitric Oxide (NO) Synthase and NO Production in a Macrophage Cell Line, RAVV264.7 Cells," American Journal of Chinese Medicine, vol. 32, No. 5, pp. 727-735,2004.
Ferrini M.G., et al., "Long-Term Continuous Treatment with Slidenafil Ameliorates Aging-Related Erectile Dysfunction and the Underlying Corporal Fibrosis in the Rat," Bioi Reprod 76:915-923, 20, 2007.
Liao, Hui et al., "Elucidattion of Danzhixiaoyao Wan and its Constituent Herbs on Antioxidant Activity and Inhibition of Nitric Oxide Production," eCam, Advanced Acess publication Jan. 9, 2007.

(Continued)

*Primary Examiner* — Susan Hoffman
(74) *Attorney, Agent, or Firm* — Welsh Flaxman & Gitler LLC

(57) ABSTRACT

Compositions for treating erectile dysfunction ("ED"), including age related erectile dysfunction (ARED), comprise in a preferred embodiment ginger and an amino acid. Preferably the amino acid is L-arginine and/or L-citrulline. Additionally, the compositions may comprise guarana (*Paullinia cupana*), Muira puama cortex magnoliae officinalis (CMO) and/or fructus aurantil immaturus (FAI). The compositions of the present inventions are administered in a pharmaceutically effective amount to treat erectile dysfunction. Essential ingredients in formulations of the present inventions for treatment of ED and ARED are ginger (or ginger derivative) and L-citrulline or L-arginine. A daily dosage of at least about 250 mg ginger and at least about 400 mg L-citrulline or L-arginine for a sufficient period of time will result in improved IIEF scores in a substantial number of patients.

17 Claims, 8 Drawing Sheets

(56) References Cited

OTHER PUBLICATIONS

Schwedhelm et al., "Pharmacokinetic and pharmacodynamic properties of oral L-citrulline and L-arginine: impact on nitric oxide metabolism," British Journal of Clinical Pharmacology, 65: pp. 51-59, (2007).

Mondiani et al."Sildenafil does not improve sexual function in men without erectile dysfunction but does reduce the postorgasmic refractory time," Int J of Imp Res. 15:225-28, 2003.

Jellin J.M., et al. Natural Product Drug Interaction Report in Pharmacist's Letter/Prescriber's Letter of Natural Medicines Comprehensive Database. Stockton, CA: Therapeutic Research Faculty; print outs from web site: https:11prescribersletter.therapeuticresearch.com This web site provides purported interactions between natural products and drugs; specifically, reported in 2005 and subsequently by Jellin, J.M., et al on this web site that Ginger interacts vvth Warfarin at doses greater than 5 g per day, accessed Mar. 2011.

Gratzke, Christian, "Daily Use of PDE5-Inhibitors: The Road to Happiness?," European Urology 54 (2008) 28-30, D available at WN'N.sciencedirect.com; journal homepage: WNVV.europeanurology.com.

Zick, Suzanna M., et al., "Pharmacokinetics of 6-Gingerol, 8-Gingerol, 10-Gingerol,and 6-Shogaol and Conjugate Metabolites in Healthy Human Subjects," Cancer Epidemiol Biomarkers Prey 2008;17:1930-1936. Published online Aug. 14, 2008.

Ferrini et al., "Treatment with a combination of ginger, L-citrulline, muira puama and Paullinia cupana can reverse the progression of corporal smooth muscle loss, fibrosis and veno-occlusive dysfunction in the aging rat,", Andrology (Los Angel), Jun. 2015; 4(1); 131.

Aktan et al., "Gingerol Metabolite and a Synthetic Analogue CapsarolTM Inhibit Macrophage NF-kB-Mediated iNOS Gene Expression and Enzyme Activity," Planta Med 2006; 72; 727-734 (May 29, 2006) [Citation D1 in corresponding Taiwan Patent Application No. 100137976].

Celso H. Oliveira et al., Clinical Toxicology Study of an Herbal Medicinal Extract, Phytotherapy Research, 2005, 54-57, John Wiley & Sons, Ltd., Wiley Interscience.

E. Antunes et al., The Relaxation of Isolated Rabbit Corpus Cavernosum by the Herbal Medicine Catuama and its Constituents, Phytother Res. Aug. 2001; 15(5):416-21.

Author Mahendra Bhaugika, Title of publication-Dhanvantarinighantaub, p. 6 (p. 4-9) ( p. 85 ), Publication Date-Edn. 3rd, 2002, Publisher-Chaukhambha Orientalia, Place of Publication-Varanasi, India.†

Author -, Title of publication-Brhat Nighantu Ratnākara (Saligramanighantubhusanam), vol. 4 (Part VII), pp. 5 (p. 10-14) (p. 674 ), Publication Date-edn. 1997, Publisher-Khemaraja Srikrsnadas Prakasana, Place of Publication-Mumbai-4, India.†

Author Mohammad Najmul Ghani Khan, Title of publication-Qaraabaadeen Najm-al-Ghani (20th century AD) (Second Edition), p. 5 (p. 15-19) ( Ref. p. 654 ), Publication Date-1928 AD, Publisher-Munshi Nawal Kishore., Place of Publication-Lucknow, India.†

\* cited by examiner
† cited by third party

International Index of Erectile Function Questionnaire questions refer to erectile function st month, how often were you able to get an erection during y?

- 0 No sexual activity
- 5 Almost always or always
- 4 Most times (much more than half the time)
- 3 Sometimes (about half the time)
- 2 A few times (much less than half the time)
- 1 Almost never or never

| International Index of Erectile Function Questionnaire |
|---|
| last month, when you had erections with sexual stimulation, how our erections hard enough for penetration?<br><br>0    No sexual activity<br><br>5    Almost always or always<br><br>4    Most times (much more than half the time)<br><br>3    Sometimes (about half the time)<br><br>2    A few times (much less than half the time)<br><br>1    Almost never or never |
| Q3. Over the last month, when you attempted intercourse, how often were you able to penetrate your partner?<br><br>       0    No sexual activity<br><br>       5    Almost always or always<br><br>       4    Most times (much more than half the time)<br><br>       3    Sometimes (about half the time)<br><br>       2    A few times (much less than half the time)<br><br>       1    Almost never or never |
| Q4. Over the last month, during sexual intercourse, how often were you able to maintain your erection after you had penetrated your partner?<br><br>       0    No sexual activity<br><br>       5    Almost always or always<br><br>       4    Most times (much more than half the time)<br><br>       3    Sometimes (about half the time)<br><br>       2    A few times (much less than half the time)<br><br>       1    Almost never or never |

FIG. 1C

| International Index of Erectile Function Questionnaire |
|---|
| last month, during sexual intercourse, how difficult was it to<br>r erection to completion of intercourse?<br><br>→ 0     No sexual activity<br>→ 1     Extremely difficult<br>→ 2     Very difficult<br>→ 3     Difficult<br>→ 4     Slightly difficult<br>→ 5     Not difficult |
| The next three questions refer to satisfaction with intercourse<br><br>Q6. Over the last month, how many times have you attempted sexual intercourse?<br><br>→    0     No attempts<br>→    1     1-2 times<br>→    2     3-4 times<br>→    3     5-6 times<br>      4     7-10 times<br>→    5     11-20 times |
| Q7. Over the last month, when you attempted sexual intercourse how often was it satisfactory for *you*?<br><br>→    0     Did not attempt intercourse<br>→    5     Almost always or always<br>      4     Most times (much more than half the time)<br>→    3     Sometimes (about half the time)<br>→    2     A few times (much less than half the time)<br>→    1     Almost never or never |

FIG. 1D

| International Index of Erectile Function Questionnaire |
|---|
| last month, how much have you enjoyed sexual intercourse? |
| 0     No intercourse |
| 5     Very highly enjoyable |
| 4     Highly enjoyable |
| 3     Fairly enjoyable |
| 2     Not very enjoyable |
| 1     No enjoyment |
| The next two questions refer to orgasmic function |
| Q9. Over the last month, when you had sexual stimulation or intercourse, how often did you ejaculate? |
|      0     No sexual stimulation/intercourse |
|      5     Almost always or always |
|      4     Most times (much more than half the time) |
|      3     Sometimes (about half the time) |
|      2     A few times (much less than half the time) |
|      1     Almost never or never |
| Q10. Over the last month, when you had sexual stimulation or intercourse, how often did you have the feeling of orgasm (with or without ejaculation)? |
|      0     No sexual stimulation/intercourse |
|      5     Almost always or always |
|      4     Most times (much more than half the time) |
|      3     Sometimes (about half the time) |
|      2     A few times (much less than half the time) |
|      1     Almost never or never |

FIG. 1E

| International Index of Erectile Function Questionnaire |
|---|
| o questions ask about sexual desire. In this context, sexual fined as a feeling that may include wanting to have a sexual (for example masturbation or sexual intercourse), thinking g sex, or feeling frustrated due to lack of sex. <br><br> e last month, how often have you felt sexual desire? <br><br>     5    Almost always or always <br><br>     4    Most times (much more than half the time) <br><br>     3    Sometimes (about half the time) <br><br>     2    A few times (much less than half the time) <br><br>     1    Almost never or never |
| Q12. Over the last month, how would you rate your level of sexual desire? <br><br>         5    Very high <br><br>         4    High <br><br>         3    Moderate <br><br>         2    Low <br><br>         1    Very low or not at all |
| The next two questions refer to overall sexual satisfaction. <br><br> Q13. Over the last month, how satisfied have you been with your overall sex life? <br><br>         5    Very satisfied <br><br>         4    Moderately satisfied <br><br>         3    About equally satisfied and dissatisfied <br><br>         2    Moderately dissatisfied <br><br>         1    Very dissatisfied |

FIG. 1F

| International Index of Erectile Function Questionnaire |
|---|
| Q14. Over the last month, how satisfied have you been with your sexual relationship with your partner? <br><br> ↓ 5 Very satisfied <br><br> ↓ 4 Moderately satisfied <br><br> ↓ 3 About equally satisfied and dissatisfied <br><br> ↓ 2 Moderately dissatisfied <br><br> ↓ 1 Very dissatisfied |
| The last question refers to erectile function |
| Q15. Over the last month, how do you rate your confidence that you can get and keep your erection? <br><br> ↓ 5 Very high <br><br> ↓ 4 High <br><br> ↓ 3 Moderate <br><br> ↓ 2 Low <br><br> ↓ 1 Very low |
| End of Erectile Function Questionnaire |

********Memorial Hospital
INSTITUTIONAL REVIEW BOARD
New Protocol Form

This form to be completed and submitted to the Institutional Review Board at HMNMH for new studies:

PROTOCOL
Title of Project: Effect of ginger, L-citrulline, muira puama and paullina cupana on men's sexual function.
Principal Investigator:_********************, M.D.____ #_____
(to be assigned by committee)

SUBJECTS RECRUITMENT

1. What is the purpose of this study? This study is being performed in an attempt to determine whether a combination of four natural products (nutraceuticals) given orally to men to help their sexual function is safe and tolerable.

2. What health information do the researchers want to use.   The main health information to be used in this study is a test called the IIEF (international index of erectile function). It tests 5 domains of a man's sexual function: erectile function, intercourse satisfaction, orgasmic function, sexual desire and overall satisfaction.   It is a validated test that is used to determine not only a man's current sexual function but the test is also used to trend changes in patient's sexual function during clinical trials.

3. Why do the researchers want this health information? This will determine whether the neutraceuticals that we are testing have any effect on the IIEF scores of these patients.

4. Who will be able to use this information?   This information from these patients will only be available to the investigators.

5. How will information be kept private? This information will be charted and kept in the patients' charts under lock and key in Dr. ***** s office.

6. Will consent form be required? Yes. See attached.

7. Approximately how many patients will participate in this study? 50 patients.

8. Approximately how long will this study take place? Each patient will be treated for 3 months.

List any other pertinent information: Male patients between the ages of 18 and 80 will be empanelled into the study. Patients who take any PDE5i or use any other aid for their sexual function will be asked to stop its use for at least 4 weeks before the start of the trial and during the 12 week trial. The study medication will be provided at no cost to the patients and they will take two pills twice per day for the entire 12 weeks of the study. They will return at 30, 60 and 90 days to fill out an IEEF form. The pills will be dispensed in bottles, each bottle enough for a 4 week's supply, at the start of, at day 30 and day 60 of the study.

FIG. 2A

| *********Memorial Hospital |
| --- |
| INSTITUTIONAL REVIEW BOARD |
| New Protocol Form |
| Committee is to be informed of all adverse events or any deviations in the protocol. If the study is longer than a year, annual progress reports are expected to be submitted to the IRB.<br><br>_____/_____<br>    Date |

FIG. 2B

COMPOSITIONS AND METHODS FOR TREATING, INHIBITING THE ONSET, AND SLOWING THE PROGRESSION OF ERECTILE DYSFUNCTION INCLUDING NATURALLY OCCURRING AGE RELATED ERECTILE DYSFUNCTION

FIELD OF THE INVENTION

The present invention relates to compositions, dosage forms and methods for treating, inhibiting the onset, and/or slowing the rate of development of erectile dysfunction ("ED"), and in particular relate to compositions, dosage forms and methods for treating, inhibiting the onset, and slowing age related erectile dysfunction ("ARED").

BACKGROUND

Impotence or erectile dysfunction (ED) is a problem that most men will face at some time in their life. In fact, by the time a man reaches 50 years of age, he has about a 1 in 2 chance of having some problem with his erection. The problem could be either attaining and/or maintaining his erection long enough to complete the sexual act. As men get older, the chance of getting ED increases such that a 60 year old man has approximately a 60% chance of having ED, a 70 year old man has about a 70% chance, etc. Even men in their 40's have about a 40% chance of having some form of ED, while it has been extrapolated that men in their 30's and 20's have about a 30% and 20% chance, respectively, of having noticed that something has changed with their erectile function.

From an anthropological or evolutionary standpoint, the demand on the reproductive organs inclusive of erectile function decreases after men pass their peak reproductive age which ranges from their late teens into their 20's. The actual age of onset of ED in an individual depends on many factors, such as genetics, health, lifestyle, etc. The major reason ED manifests itself, regardless of the age of onset, is due to an alteration in the corporal cavernosal smooth muscle (CSM), which is located within the cavernosal or corporal bodies of the penis.

The function of the CSM in the erectile process is to receive and trap blood entering the corporal bodies. This is accomplished when the CSM undergoes relaxation that allows it to open up and create spaces or sinusoids into which the entering blood pools. The pooling of this blood in sinusoidal spaces increases the pressure within the corporal bodies and when a certain intracorporeal pressure is reached, the pressure closes off the veins that drain the blood out of the corporal bodies, essentially trapping it within the corporal bodies. Clinically, this is how the CSM tissue is able to attain (by creating spaces for the blood to pool into) and maintain (by closing off the veins) an erection. It is when this CSM begins to degrade in some way or another and becomes incapable of either relaxing sufficiently enough to create these spaces where the blood is normally trapped or it cannot maintain its relaxation long enough so that it fails to compress the veins that provide egress for blood from the corporal bodies that ED begins to be manifested. While some men may not notice signs of ED until later in life, it is inevitable that ED will occur if one lives long enough.

There are multiple biochemical pathways involved in penile erection and dysfunction. Without stimulation, flaccidity can be considered as the baseline state. Flaccidity is due to corpus cavernosum smooth-muscle cells ("CSM") being contracted and helicine arterioles being sufficiently contracted to limit blood flow to corpus covernosal sinuses; the sympathetic nervous system and tonic adrenergic discharge maintain baseline contraction of smooth muscle cells and arteriole blood supply (e.g., adrenergic, cholinergic, and nonadrenergic-noncholinergic pathways). So, a combination of metabolic pathways are involved in inducing the erectile processes involving smooth muscle relaxation, arterial dilation, and venous occlusion.

As noted above, by age 50 about one half of all men will have noticeable ED. The presence of certain diseases, e.g. diabetes, or certain lifestyles, e.g. smoking, may accelerate in time the genetically predetermined onset of the degradation of the CSM such that men with diabetes tend to get ED at a younger age when compared to non-diabetics. It is believed that the degradation of the CSM is ultimately the result of oxidative stress; this oxidation process within the CSM is accelerated by certain diseases (e.g. diabetes), and lifestyles (e.g. smoking), etc. Oxidation of this tissue ultimately results in a progressive loss of the CSM cells and a corresponding increase in collagen fibers or fibrous tissue. At a certain level of loss of the CSM within the corporal tissue, which some estimate to be between 10 and 20% of the CSM cells, the impact on erectile function becomes noticeable. The first recognition that one's erectile mechanism is worsening is the increase in time that it takes for one to achieve subsequent erections. This time in between subsequent erections is called the refractory period and it is the first indication that the CSM tissue is changing for the worse.

When the CSM cells begin to undergo oxidation and deteriorate either as a result of aging or some other cause, the CSM begin to induce an enzyme called inducible nitric oxide synthase (iNOS) which produces nitric oxide in high quantities within the cells that begins to combat the oxidative stress. This induction of nitric oxide (NO) by iNOS is different from the NO that is found in the nerves of the body including the nerves that innervates the CSM cells. This NO in the nerves is produced by a related enzyme, neuronal nitric oxide synthase ("nNOS"), and in the penis it only releases NO when the patient is sexually stimulated. This NO from nNOS is the major chemical that is involved in the relaxation of the CSM cells and hence is required for the initiation and maintenance of a normal erection. Therefore, while nNOS is normally present in the nerves innervating the penis, iNOS is normally not present in the CSM cells of the penis and is only induced by the CSM cells themselves when the cells experience oxidative stress. However, when iNOS is induced as seen in U.S. Pat. No. 5,594,032, human erectile dysfunction can be ameliorated by treatment with iNOS, inducers of iNOS or iNOS cDNA. Further background on sexual dysfunction, urogenital disease, ED and treatments therefore can be found in U.S. Pat. Nos. 6,133,281, 6,007,824, U.S. Patent Publication 2005/0085486, and Schwartz, Eric, et al., "Sildenafil Preserves Intracorporeal Smooth Muscle After Radical Retropubic Prostatectomy," *The Journal of Urology*, Vol 171, pp. 771-774, February 2004.

With reference to U.S. Patent Publication 2005/0085486, fibrotic disease is linked to reproductive disorders and cardiovascular disease, which are both prevalent in aging males. The ubiquitous and long felt need to treat sexual dysfunction has led to surgical and pharmacological treatment approaches. The ongoing commercial success of prescription medications under the trademarks VIAGRA®, LEVITRA® and CIALIS® for treatment of ED demonstrates the long felt and widespread need for effective treatments for ED, particularly for patients that present with ED symptoms advanced sufficiently that erections of satisfactory duration at the desired time can only be reliably accomplished by taking the prescription drug.

Thus, there remains a ubiquitous and long-felt need to treat ED before it progresses to the point where pharmacological and/or other medical intervention is required in order to have desired sexual performance. Nevertheless, current ED drugs, such as VIAGRA® and CIALIS®, are generally prescribed only after the patient has presented with symptoms of ED. These drugs belong to a class of drugs called Type 5 phosphodiesterase (PDE5) inhibitors. PDE5 is an enzyme that breaks down cGMP once it is formed and PDE5 inhibitors like Viagra, Clalis and Levitra prevent the cGMP from breaking down so the effect of the cGMP on the tissues is enhanced. With regards to erectile function, cGMP is formed within the CSM from a reaction that is initiated by the NO that is released from the cavernosal nerve following sexual stimulation. The NO that begins the erectile response comes from the enzyme nNOS that is located in the nerve endings. The NO enters the CSM cells and causes a reaction to occur. NO activates the enzyme soluble guanylyl cyclase (sGC) in the cytoplasm of the CSM and this enzyme in turn converts guanosine triphosphate (GTP) into cyclic guanosine monophosphate (cGMP). An increase in cGMP stimulates protein kinase G to phosphorylate potassium and calcium channels causing a decrease in cytosolic calcium, dilation of the helicine arterioles, and the relaxation of the trebecular smooth muscle where all the CSM cells are located. As noted above, the relaxation of the smooth muscle leads to an increase in the intracavernosal volume, initiating the erectile process. Normally, endogenous PDE5 enzyme degrades cGMP which reverses the relaxation of the smooth muscle cells, and leads to loss of erection whereas the ingestion of these PDE5 inhibitors prior to sexual stimulation prevent the degradation of the cGMP that is formed thereby prolonging any CSM relaxation and enhancing any erectile response.

Currently, one suffering from ED needs to see a doctor and get a prescription for an ED treatment in advance in order to be prepared for a satisfying experience. Onset and duration of the effects of PDE5 inhibitors like Viagra, Clalis and Levitra depend on the specificity of the compound. While PDE5 inhibitors are considered the "first line treatment of ED," there are notable side effects (headache, flushing, dyspepsia, rhinitis, visual disturbances, back pain, etc.) and adverse interactions that can limit or bar their use (e.g., patients taking nitrates with a PDE5i can experience hypotension and syncope. See Dorsey, Philip et al., "Phosphodiesterase type 5 (PDE5) inhibitors for the treatment of erectile dysfunction," *Expert Opinion, Pharmacother.* (2010), 11(7): pp 1109-1122). Since most men will at some time in their life get ED mainly as the result of CSM deterioration secondary to the aging process, the present inventor faced the problem of whether or not it is desirable to treat men who are asymptomatic but whose refractory period has begun to increase—a subtle sign that the CSM is beginning to undergo deterioration—in order to slow or prevent the progression of this deterioration and the forthcoming ED. For patients who already have noticeable ED symptoms, it may also be desirable to slow if not stop or reverse the progression of the ED.

Prior research indicated that high doses of ginger combined with the iNOS stimulant lipopolysaccharide (LPS) could increase nitric oxide production. However, this conflicted with other work that indicates that ginger by itself and without LPS stimulated iNOS production in a dose dependent manner and in much lower doses (see *American Journal of Chinese Medicine*, Vol. 32, No. 5, pp 727-735, 2004). Use of high dosages of ginger are impractical for long term routine administration, so initially the present inventor focused on isolating specific compounds within ginger, such as 6-gingerol, that might be utilized in a formulation for stimulating iNOS. However, use of such specific compounds is more expensive, and ginger by itself was insufficient to provide a reasonable alternative to PDE5 inhibitors to treat and/or prevent ED.

Numerous natural products, such as ginseng, are claimed to have "tonic" or "adaptogenic" properties. A tonic or adaptogenic effect is characterized as a general feeling of vigor or well-being that is purportedly the result of taking natural herbs, such as ginseng, ginko balboa, etc. Traditional Chinese folk medicine includes numerous teachings of herbal formulations having different purported properties. However, natural herbs are often complex mixtures, and have different names and chemical formulations depending on the geographic source. The mixture of the main or named ingredient with other ingredients and conflicting reports of the effects of same requires that careful scientific studies be conducted to determine the properties of each ingredients in an herb on specific aspects of health. The use of natural herbs in treating disease cannot be reliably predicted on the basis of folk lore.

For example, Withania somnifera, a plant in the Solanaceae or nightshade family, is also known as Ashwaganda, Indian ginseng, Amukkara in Tamil, etc. Ginseng or Ashwagandha is widely promoted for a wide variety of uses, including as an aphrodisiac or for increasing male sexual performance, alone or in combination with other ingredients. in Japanese patent application 2002-193826, to Kosuke, a combination of 1 gram of ashwaganda with 1 gram arginine or of 1 gram of ashwaganda and 1 gram of oat extract is taught as a tonic or adaptogenic composition that can increase erectile function; with daily use for 90 days, increases in sperm count and erections were reported. The essential ingredient taught by Kosuke to improve erectile function is ginseng (or Ashwaghandha). One formulation of Kosuke includes ashwagandha, arginine, and yeast with zinc; the zinc is purported to help increase sperm count. In addition to ashwagandha and/or oat, Kosuke suggests addition of at least one of eight other natural products: velvet bean, cola, guarana, ginko leaves, kava kava, maca, ginger and extracts thereof for different purposes. For example, ginger is a suggested additional ingredient for "stimulating the central nerve and thereby having a perspiration action and a blood flow stimulation action." However, ginger is also taught by the prior art to adversely effect the nitric oxide metabolism involved in erectile function; see Liao, Hui et al., "Elucidation of Danzhixiaoyao Wan and its Constituent Herbs on Antioxidant Activity and Inhibition of Nitric Oxide Production," *eCam*, Advanced Access publication Jan. 9, 2007), i.e., ginger is taught to cause, not treat, erectile dysfunction. Thus, one would not be led to add ginger to Kosuke's formulation that requires ginseng and that purports to increase erectile function in view of other teachings that ginger has an adverse effect on erectile function; such reports of ginger's adverse effect on erectile function would not outweigh Kosuke's suggestion to use ginger for a generalized tonic effect, not erectile function.

The listing of a wide variety of different compositions of natural products with unverified benefits, such as by Kosuke, can be risky to persons taking them. Sometimes one herb ingredient counteracts another, the formulation does not result in the claimed benefit, and/or in some instances medical conditions can be overlooked or made worse.

With respect to ginseng, its purported effect on sexual function may be due to impact on nitric oxide production, while arginine is also believed to play a role in endogenous nitric oxide metabolism. Nevertheless, ashwagandha or ginseng has not proven to have a sufficient benefit in the treatment of erectile dysfunction. Further, complex formulations including ginseng and a "shotgun" approach to adding up to eight different ingredients (or more) for purported enhancement of a tonic effect is not a reliable indicator that any product, natural or synthetic, has a beneficial impact on the patient or particular symptom being treated. Moreover, a tonic benefit may arise from the patient having increased food intake as a result of taking the compositions, and therefore the recipient may simply have more energy or good health resulting from caloric, vitamin and protein ingestion from their overall diet. The addition of various other ingredients without having reliable data on which ingredients have the purported benefit, while other ingredients may have their effects covered up or misinterpreted, makes it practically impossible to medically rely on generalized suggestions. Kosuke gives examples of tests with formulations that contain ashwagandha and arginine, but formulations with other ingredients were not tested for the purported effects they would bring. While the prior art suggests that ginseng may enhance erectile function, the benefits thereof have not been sufficient to replace treatment with existing erectile dysfunction drugs, such as PDE5 inhibitors, particularly for patients that are showing increases in the refractory period between erections and other symptoms indicative of progressive erectile dysfunction.

The science behind the use of dietary supplements to treat diseases has increased over the past several decades. This includes the use of natural foods or products in combination with specific compounds. For example, arginine and other amino acids have been known for decades to play important roles in biological function of humans and animals in general, however, the biological and biochemical roles are still being elucidated so that significant unpredictability remains for even small changes in formulations and/or depending on varying patient specific factors. Ginger and other herbs are often combined in foods. A combination of rosemary with other ingredients (e.g., curcumin and guercitin) is taught in U.S. Patent application 2002/0051826 to Darland et al for use in treating inflammation-related diseases. In addition to those main ingredients, Darland also suggests optionally using limonene, which can come from D-limonene or hesperidin, or the use of between 180 mg and 220 mg of ginger; the formulation can optionally include 180 mg to 220 mg of citrulline and other vitamins. Such reports indicate the safety of ingredients such as ginger, citrulline and arginine as long-term dietary supplements. While, such complex formulations are indicated to have general health benefits, there is a need for increased testing of specific formulations and determination of their impacts, both positive and negative, on different aspects of health.

Thus, there remains substantial unpredictability in the benefits and detriments of natural herbs, with a wide range of conflicting and unreliable teachings, many based on anecdotal reports that cannot be reliably reproduced. In order to make a medical treatment recommendation, one of ordinary skill in the art of Western medical research, requires data from studies that used accepted scientific methods. Such scientific methods include controls (e.g., placebo or base line formulations), independent objective analysis, patient histories and patient monitoring before, during and after each study, where possible double blind clinical trials, and uniform compositions with reliable and consistent ingredients and analyses. Otherwise, the data or conclusions are subject to criticism as subjective, anecdotal, and/or wrong based on properly conducted studies, for example studies of the type accepted by the U.S. Food and Drug Agency (US FDA), which may include an IRB protocol (Institutional Review Board protocol submitted to and approved by other scientists). It is desired to have study results that can be relied upon by clinicians trained in modern medicine and science in the United States, Europe, Canada, China, Japan, and other countries. While it is desirable to use natural products that have well-established safety as foods in place of synthetic chemical pharmaceutical formulations, such use must be based on sufficient studies to justify replacing or supplementing medicines that have met regulatory and scientific scrutiny. The present inventor was challenged by the problems of finding compositions and methods for treatment and inhibition of ED that are practical for long term routine administration, while avoiding side effects of existing formulations, enable treatment of and prevention of ED in patients that cannot utilize prior art ED treatments, and/or provide new practical and cost effective compositions to prevent as well as treat ED. Preferably, such formulations are simpler and do not include ginseng, rosemary and/or ingredients that have not been demonstrated to have a sufficient and consistent clinical benefit for the treatment of ED.

SUMMARY OF THE INVENTION

According to a first aspect of the present invention, there is provided a pharmaceutical composition comprising an effective amount of:
 ginger or a ginger derivative selected from the group consisting of fresh, partially dried vegetable ginger, dried vegetable ginger, 6-gingerol and mixtures thereof; and
 at least one of group consisting of arginine and citrulline, and wherein preferably the composition comprises at least one of the group consisting of L-arginine and L-citrulline.

By effective amount, a dosage form of the composition contains an amount of each ingredient sufficient when administered for a sufficient period of time to produce a beneficial effect in treating ED or ARED, wherein the beneficial effect includes at least one of slowing, stopping or reversing worsening symptoms of ED or ARED, slowing, stopping or reversing the appearance of symptoms of ED or ARED, shortening refractory period between erections, and/or reducing, slowing or stopping increases in refractory period between erections. In an embodiment, indicia of ED or ARED are treated and/or indicia of satisfactory sexual experience are improved, for example duration and/or reduction or elimination of pain during or following sexual activity.

A preferred embodiment of a pharmaceutical composition in accordance with the first aspect of the present inventions is characterized in that it comprises:
 a dosage form having at least 250 mg ginger or ginger derivative, and an effective amount of L-citrulline, wherein said composition can be administered in periodic dosages for a sufficient period of time to treat erectile dysfunction or age related erectile dysfunction.

An alternative preferred embodiment of the pharmaceutical composition of the first aspect of the present inventions is characterized in that it comprises:

a dosage form having at least 250 mg ginger or ginger derivative, and an effective amount of at least one of group consisting of L-citrulline and L-arginine, said composition preferably having the essential absence of ginseng, wherein the ingredients essential for treating erectile dysfunction in said dosage form are said ginger and at least one member of the group consisting of L-citrulline and L-arginine. wherein said composition can be administered in periodic dosages for a sufficient period of time to treat erectile dysfunction or age related erectile dysfunction.

In a preferred embodiment, the forgoing dosage forms comprise at least about 400 mg of a composition consisting of at least one of L-citrulline and L-arginine. Such a composition can be administered at least once a day for a sufficient period of time to treat ED or ARED.

The compositions or dosage forms may include optional pharmaceutically acceptable excipients, fillers, binders, and colorants, and can be packaged in standard gelatin capsules or formed into solid tablets, taken in particulate form, or mixed into and/or suspended in solution. In compositions of the present inventions ginger and arginine or citrulline are the primary active ingredients for producing the beneficial effect on ED or ARED from their use, so that the compositions have the desired benefit in treating ED in the essential absence of ashwagandha (ginseng) and/or rosemary. In other words, preferred compositions of the present invention do not contain an amount of ginseng (ashwagandha) effective in treating ED or ARED. Preferably, when determining the efficacy of a composition of the present invention in treating ED or ARED by IIEF score, a composition containing no ginseng would have the same effect on ED or ARED than a substantially identical formulation to which some amount of ginseng is included, i.e., such a formulation would not therefore have an effective amount of ginseng. In another embodiment, preferred compositions of the present invention do not contain rosemary.

The ginger or ginger derivative is preferably derived from *Zingiber officinale roscoe*. The derivative may comprise or is derived from rhizomes of *Zingiber officinale roscoe*. Preferably, in a daily dosage form of the composition, ginger is present in an amount of at least about 250 mg and arginine or citrulline is present in an amount of at least about 400 mg, along with other optional ingredients, such as a binding agent, an agent that increases dissolution and digestion in vivo, preservatives and/or colorants. The composition preferably contains no ashwagandha (ginseng), oat or oat extract, and/or rosemary, so that an effective amount of said composition produces the desired effect(s) in the absence of ashwagandha (ginseng), oat or oat extract and/or rosemary. While lesser amounts per day of each ingredient in the composition may have the desired beneficial effect, in order to have desired results the present inventor has determined that a daily dosage of at least about 250 mg ginger, preferably in the form of ginger root extract or the equivalent quantity of another ginger compound, provides the benefits for medicinal and nutritional recommendations to treat ED and ARED.

A second aspect of the inventions comprises the use of ginger and at least one of the group consisting of L-arginine and L-citrulline for the manufacture of a medicament for treating erectile dysfunction (ED) or age related erectile dysfunction (ARED) in the essential absence of ashwagandha (ginseng). Preferably, also absent are oat, oat extract, and rosemary. The medicament is characterized in that the composition comprises an effective amount of ginger, at least one of the group consisting of L-arginine and L-citrulline, in the essential absence of ashwagandha. Should rosemary be present, at least about 250 mg ginger is present in a daily formulation. By essential absence is meant that the composition has the desired medicinal property without the presence of ashwagandha and rosemary, so that the addition of such ingredients is not necessary for desired treatment endpoints to be reached. These medicaments reflect the inventors surprising discovery that a combination of ginger and L-citrulline or L-arginine can treat ED and ARED, and even reverse physiological processes that cause ED and ARED, so that the beneficial results may continue for a period of time after administration. Nevertheless, the composition may be taken for an indefinite period to sustain the beneficial effects and/or to postpone or reduce progression of ED or ARED.

The amount of ginger in a safe daily formulation can be about 1 mg to about 2 g or more, preferably from about 10 mg to about 3 g, most preferably from about 250 mg to about 2 g. For example, in a preferred embodiment, the daily dosage form comprises at least about 250 mg ginger or 250 mg ginger root extract or other ginger derivative and at least about 800 mg L-citrulline, and is administered twice a day at least for a sufficient period of time for the desired effect on ED or ARED to be noted. Preferably, the formulation is administered for a sufficient number of days to lead to an improvement in erectile function that is measured by the International Index of Erectile Function Questionaire. For prophylaxis, the IIEF scores over a period of time should demonstrate no or a reduced rate of change for patients taking the medicament versus patients not taking the medicament. For patients that demonstrated progression of ED or ARED by IIEF scores prior to taking the medicament, changes with treatment over time may be determined by a slowing, stopping or reversal of IIEF scores.

In a third aspect of the present inventions the composition of ginger and at least one of the group consisting of L-arginine and L-citrulline further comprises Muira puama (muira puama) and/or *Paullinia Cupana* (*paullinia cupana* or guarana). Guarana formulations used in making compositions of the present inventions may optionally include caffeine.

The amount of arginine or a compound that can produce arginine in vivo in a daily formulation is preferably from about 400 mg to about 3 g. Preferably, the arginine is L-arginine and the compound that can produce arginine in vivo is citrulline, preferably L-citrulline. Some or all of the L-arginine can be replaced with L-citrulline. In an embodiment, the daily dosage form is divided, so that patients are administered the formulation twice a day until the desired effect or end point is achieved and/or the administration continues indefinitely, and preferably the patient receives daily at least 500 mg ginger, ginger root extract or other ginger derivative having the desired effect.

According to a fourth aspect of the present invention, an oral dosage form comprises a composition in accordance with the first, second and third aspects of the inventions, wherein the dosage form is selected from the group consisting of a tablet, capsule, lozenge, powder or suspension comprising the foregoing ingredients. Preferred suspensions are aqueous and/or alcohol (ethanol) based.

According to further aspects of the inventions there is provided a composition (dosage form) in accordance with the fourth aspect of the invention for use in treatment of erectile dysfunction or age related erectile dysfunction.

According to a fifth aspect of the invention there is provided use of a plant or plant derivative selected from the group consisting of fresh, partially dried or dried ginger, 6-gingerol and mixtures thereof and an additional compound selected from the group consisting of at least one of L-arginine and L-citrulline for manufacturing a medicament for simultaneous, separate or sequential application for treating erectile dysfunction by administration of from 100 mg up to 2 g of ginger or a ginger derivative (said ginger derivative can be derived from the group consisting of fresh, partially dried or dried ginger, 6-gingerol and mixtures thereof), and 100 mg to 3 g of at least one of the group consisting of L-arginine and L-citrulline for treatment of erectile dysfunction. The treatment essentially requires ginger and at least one of L-citrulline and L-arginine, wherein ginseng and is absent. Preferably, said dosage form comprises at least about 250 mg ginger or ginger derivative and at least about 400 mg of L-citrulline or L-arginine or a mixture thereof; said dosage form can be administered at least once a day, preferably twice a day, for a sufficient period of time to treat erectile dysfunction or age related erectile dysfunction. Preferably, monitoring and treatment of erectile dysfunction is by IIEF scores.

The composition of matter derived from *Zingiber officinale* roscoe may comprise fresh roots or stem parts, preferably rhizomes. The matter may be used fresh or may be partially or completely dehydrated. Fresh natural products used for ingredients of the present invention may be chopped, pulped or otherwise comminuted before incorporation into a dosage form. For example, an ingredient may be concentrated to facilitate transportation, storage, and administration.

The raw materials and ingredient matter may be dried, for example by freeze-drying or vacuum drying, before compounding into oral dosage forms. Individual dosage forms may comprise compressed tablets, capsules, lozenges or may be provided in sachets. Suspension formulations may be provided. Ginger, ginger root extract, L-arginine, L-citrulline, muira puama and *paullinia cupana* are all separately commercially available, with preferred sources and analyses provided infra. Preferably, the ingredients are combined and encapsulated in gelatin capsules, but other dosage forms are anticipated that will produce equivalent results.

Flavorings or taste masking agents may be employed. Tablets or other dosage forms may include diluents (for example lactose), disintegrants, for example cross carmelose sodium or binders, for example, polyvinylpyrollidone. Lubricants for example magnesium stearate, or other conventional excipients may be employed (e.g., silicas, carbohydrates, etc.). Film coated tablets may be provided.

The present inventor discovered that ED is arrested, inhibited, and even reversed in some instances by use of a composition of the present inventions and methods of treatment utilizing same. In vitro experiments have established that when inducible nitric oxide synthase ("iNOS") is stimulated on a daily basis when the penile musculature is deteriorating (e.g., from oxidative stress), penile muscle loss can be inhibited and in some instances new penile muscle tissue forms to replace lost muscle (Ferrini et al. Biol Reprod 76:915-923, 2007). Thus, in an embodiment, iNOS stimulation is utilized to treat and/or prevent ED. The inventor also discovered that, to optimize results, the dosages and ingredients of the compositions of the present inventions should be varied depending on the age of the patient or on the onset of ED symptoms. The compositions of the present inventions are particularly useful in the treatment of ARED. The present inventor has surprisingly discovered that dosages of ginger small enough to be useful and practicable in routine, even daily, administration over an extended period of time can be used in compositions of the present invention for treating and inhibiting ED.

Preferred compositions include ginger, and L-arginine or L-citrulline. In an embodiment, a composition for the treatment and prevention of ED comprises ginger and L-citrulline. Treatment for ED includes repeated administration of the compositions of the present inventions to a patient over a period of time sufficient to obtain the desired result. Preferred compositions of the present inventions may not contain compounds that require a prescription and/or avoid side effects of current "first line" treatments for ED. More details of exemplary embodiments of the present inventions follow.

BRIEF DESCRIPTION OF THE DRAWINGS

FIGS. 1A-1F cumulatively show a questionnaire for obtaining "IIEF scores."

FIGS. 2A-2B cumulatively show a Protocol Form in accordance with the present invention.

FURTHER DETAILS OF THE INVENTION

Experiments in vitro demonstrated that ginger, also known as *Zingiber officinale roscoe* (ZOR), at low dosages in the presence of LPS did not appear to stimulate iNOS production. However, the present inventor made the surprising discovery that at higher dosages extracts or vegetable matter derived from ZOR, e.g. 500 mg/L, in the presence of LPS stimulates iNOS. The present inventor also surprisingly discovered that vegetable matter derived from ginger, without separating its ingredients and without the presence of LPS, can cause sufficient stimulation of iNOS to enable much lower dosages of ginger to be used effectively in compositions of the present inventions to treat and prevent ED. For example, in Table 1 below are presented nitrite production data from in vitro experiments with cells incubated with varying amounts of ginger without LPS.

TABLE 1

EFFECT OF GINGER ON NITRIC OXIDE PRODUCTION
Cells incubated with differing concentrations of ginger in the absence of LPS

|  | Ginger concentration (mg/L) | Nitrite Production (micromolar) |
| --- | --- | --- |
| Control | 0 | $0.8 \pm 0.1$ |
| Fresh Ginger | 50 | $36.1 \pm 4.2$ |
| Fresh Ginger | 500 | $219.8 \pm 7.3$ |
| Dried Ginger | 50 | $40.8 \pm 2.1$ |
| Dried Ginger | 500 | $207.7 \pm 28.0$ |

The nutraceutical or pharmaceutical compositions of the present inventions are administered in a pharmaceutically effective amount to treat erectile dysfunction. Treatments can consist of either short term self administered oral dosages taken periodically, e.g. at least once a day or other period of time in between dosages until the desired effect is reached or as part of one's long term, even life time, daily nutrition.

The present inventor found with in vitro experiments that dosages of ginger low enough to be practicable for routine administration are capable of use to treat ED when used in the compositions and methods of the present inventions. Also, by varying the ratio of ginger to other ingredients, the formulations and dosing schedule can be optimized for specific patients and/or patient profiles. One method to determine patient profiles is by obtaining a biopsy of the penile tissue to evaluate the integrity of the CSM cells.

Obtaining biopsy specimens of penile tissue can be performed in a relatively painless manner, either during the performance of other surgical procedures e.g. during prostate surgery or even an office visit at which an analgesic/local anesthetic can be used prior to the biopsy. See Schwartz, Eric, et al., "Sildenafil Preserves Intracorporeal Smooth Muscle After Radical Retropubic Prostatectomy," *The Journal of Urology*, Vol 171, pp. 771-774, February 2004. In the alternative, blood or other non-penile tissue may be obtained for DNA analysis. Patients at risk for developing ED can be identified by these various methods. Whether via biopsy or other means e.g. DNA analysis, patients susceptible to ED can be identified and treatment with formulations of the present invention or other treatments can be started prior to ED symptoms becoming sufficient to interfere with normal sexual function. In fact, in some cases it is believed that a decrease in smooth muscle cells may be reversed sufficiently to allow patients to improve their erectile function.

In an embodiment, erectile function can be monitored via the International Index of Erectile Function Questionnaire. By use of this standard questionnaire, a large number of patient histories, with identities redacted, can be combined with questionnaire results to generate statistically significant data when compared with questionnaire results following administration of different compositions (or placebo). Presented FIGS. 1A-1F is a questionnaire for use in obtaining "IIEF scores":

In an embodiment, a composition for the treatment of erectile dysfunction may further include cortex magnoliae officinalis and/or fructus aurantii immaturus (also referred to hereinafter as "CMO" and "FAI" respectively). While not wishing to be limited to a particular theory of pharmacologic action, these compounds stimulate nitric oxide). Thus, the beneficial agents in the compositions of the present inventions for treatment of ED and/or ARED are ginger, at least one of L-arginine and L-citrulline, muira puama, *paullinia cupana*, CMO and FAI. However, the first two ingredients (ginger and at least one of L-citrulline and L-arginine) are essential in the compositions and their ability to treat ED and ARED.

Ginger is a complex natural composition having numerous purported properties when used alone and/or combination with other compounds. For example, traditional Chinese medicines have used or included ginger in compositions to treat or prevent various maladies based on a variety of metaphysical reasons. Over the past century, scientific methods have shown that many traditional Chinese medicines do not produce the purported effects and/or may even make the target maladies worse. Nevertheless, some traditional Chinese medicines have been found to contain active agents that may be of medical use, even if not effective or safe for the use purported by traditional Chinese medicine. The complexity of ginger and its myriad properties is reflected by certain constituent compounds which have the following structure:

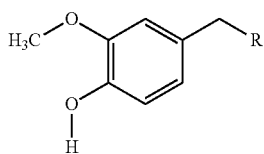

wherein, for example, in 6-gingerol the R sidechain of the vanillyl function group (i.e., 4-hydroxy-3-methoxyphenyl group) is:

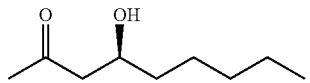

Thus, 6-gingerol (also called gingerol) is (S)-5-hydroxy-1-(4-hydroxy-3-methoxyphenyl)-3-decanone and has the following structure:

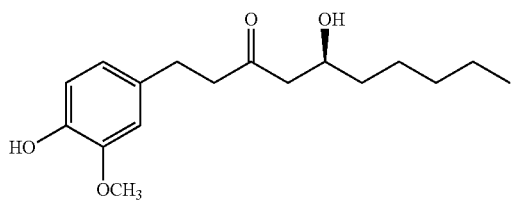 [SMILES: CCCCC[C@H](O)CC(=O)CCc1ccc(O)c(OC)c1]

Since ginger contains multiple compounds, of varying complexity and chemical activity, there are multiple biochemical pathways involved in erectile function and dysfunction, and there are conflicting teachings in the prior art about the biological activity of compounds that might be useful in inducing NO production or otherwise having a potential role in treatment, there remains considerable unpredictability about how to understand, much less control, the relevant metabolic pathways. In fact, the prior art teaches that compositions that contain ginger, for example Danzhixiaoyao Wan, actually inhibit nitric oxide production, i.e., could cause erectile dysfunction (see Liao, Hui et al., "Elucidation of Danzhixiaoyao Wan and its Constituent Herbs on Antioxidant Activity and Inhibition of Nitric Oxide Production," *eCam*, Advanced Access publication Jan. 9, 2007). Nevertheless, the same article indicates that ZOR (ginger) at 500 mg/L "seemed to stimulate nitric oxide production" but had no effect at 50 mg/L. In contrast, the present inventor has surprisingly discovered that ginger at low doses in compositions of the present invention can be effectively used to treat ED.

Preferred amounts of ginger in compositions of the present invention comprise between about 1 mg and about 2 grams. The compositions further comprise about 10 mg to about 2 grams L-citrulline. About 10 mg to about 2 grams L-arginine can be used in place of and/or in addition to L-citrulline. However, since it has been discovered that a larger amount of in vivo L-arginine for use in endogenous production of NO can be induced by a smaller dosage of L-citrulline than of oral L-arginine, preferred compositions of the present invention include L-citrulline in place of and/or in addition to L-arginine (see Schwedhelm et al., *British Journal of Clinical Pharmacology*, 65: pp 51-59, (2007)).

A preferred composition for treatment of penile muscle degradation in men that do not exhibit substantial or noticeable symptoms of ED contains about 100 milligrams to about 2 grams ginger and about 500 milligrams to about 3 grams of L-citrulline. An alternative composition comprises about 100 milligrams to about 2 grams ginger and about 500 milligrams to about 3 grams of L-arginine. While the present inventor has found a composition using 210 milligrams of 6-gingerol (85%) to about 1 gram of L-arginine to be effective, as noted above the use of ginger is preferred as it has been found to be effective at surprisingly low dosages in compositions of the present invention. Compositions of the present inventions are also useful in treatment of men of any age whether or not ED symptoms are noticeable. As used herein, treatment includes slowing or inhibition of further deterioration of the penile corporal cavernosal smooth muscle even when symptoms of ED are not noticeable. Repeated dosages of compositions of the present inventions can be provided over extended periods of time until the desired effect is obtained. Repeated administration of the compositions of the present inventions to patients demonstrating ED symptoms can be made until desired ED treatment results are obtained, and may be continued thereafter as a prophylactic. The compositions can also be used as a prophylactic against eventual ED symptom manifestation in patients likely to demonstrate same.

It is believed that the fibrotic processes within the penis that are associated with ED may begin at any age. Administration of the compositions of the present invention to a patient that has not noticed an increase in the refractory period, decrease in duration of erection, and/or insufficient tumescence of erection may also be referred to as preventing ED. However, since almost all men will ultimately develop some form of ED with age, and by age 40 a significant percentage of men experience noticeable symptoms of ED, what may be referred to as prevention is likely a treatment that slows or stops further progression of the causes of ED. Preferably, as part of a daily vitamin or other nutrition routine, a pharmaceutically effective amount of compositions of the present invention are taken regularly, if not daily, by males beginning at age 20 or earlier.

For patients that have noticeable symptoms of ED, regardless of age, or for older males, whether or not symptomatic, a preferred nutraceutical composition comprises ginger, L-arginine and/or L-citrulline, FAI, CMO, *Paullinia cupana*, and Muira puama. A preferred first composition for administration at least once a day comprises ginger and at least one of L-arginine and L-citrulline, and has an essential absence of ginseng (ashwagandha), oat, oat extract and rosemary. A preferred second composition for administration at least once a day comprises at least 250 mg ginger and at least one of L-arginine and L-citrulline, and has an essential absence of ginseng (ashwagandha), oat, and oat extract, A preferred third composition of the present invention for administration at least once a day comprises ginger, at least one of L-arginine and L-citrulline, and at least one of muira puama and *paullinia cupana*. The third composition may further comprise at least one of FAI and CMO.

A preferred ingredient source for clinical trial formulations, discussed infra is Nature's Products, Inc., of Sunrise Fla., USA.

The active ingredients of compositions of the present invention can be combined using well known and standard processes and agents. Preferably, a gelatin capsule contains the combined ingredients in powder form. Standard ingredients in powder formulations are used for preparing and compounding preferred exemplary formulations of the present inventions. For example, carrier silica (e.g., Spernat 50S® from Evonik Degusa Industries of Parsippany, N.J., USA) can be used to convert liquids into free flowing powders and/or can be used to enhance flowability and shelf life of powdered products (especially powders prone to caking). Magnesim stearate (octadecanoic acid, magnesium salt, e.g., LIGAMED from Peter Greven of the Netherlands) can be used as a diluent with lubricating properties helpful to prevent the composition and its ingredients from sticking to manufacturing equipment, and can also serve as a binding agent. Exemplary compositions for Base formulations 1, 2 and 3 are presented below. The ingredients, in powder form, are inspected, weighed, blended and encapsulated in gelatin capsules. The blending process includes standard screening, blending and metal detection at standard temperatures and in a sterile environment at least sufficient for food supplements.

| BASE FORMULATION 1 CAPSULE NET WEIGHT 1070 MG #00 GELATIN | |
|---|---|
| | AMOUNT |
| ACTIVE INGREDIENTS | |
| L-CITRULLINE | 400 mg |
| GINGER ROOT EXTRACT, 5% GINGEROLS | 250 mg |
| OTHER INGREDIENTS | |
| MAGNESIUM STEARATE (VEG) | |
| SILICON DIOXIDE | |
| TITANIUM DIOXIDE | |
| FD&C BLUE #1 | |

| BASE FORMULATION 2 CAPSULE NET WEIGHT 545 MG #00 GELATIN | |
|---|---|
| | AMOUNT |
| ACTIVE INGREDIENTS | |
| L-CITRULLINE | 400 mg |
| GINGER ROOT EXTRACT, 5% GINGEROLS | 125 mg |
| OTHER INGREDIENTS | |
| MAGNESIUM STEARATE (VEG) | |
| SILICON DIOXIDE | |
| TITANIUM DIOXIDE | |
| FD&C BLUE #1 | |

| BASE FORMULATION 3 CAPSULE NET WEIGHT 795 MG #00 GELATIN | |
|---|---|
| | AMOUNT |
| ACTIVE INGREDIENTS | |
| L-CITRULLINE | 400 mg |
| GINGER ROOT EXTRACT, 5% GINGEROLS | 125 mg |
| GUARANA EXTRACT, 8% CAFFEINE (from seed) | 125 mg |
| MUIRA PUAMA 4:1 | 125 mg |
| OTHER INGREDIENTS | |
| MAGNESIUM STEARATE (VEG) | |
| SILICON DIOXIDE | |
| TITANIUM DIOXIDE | |
| FD&C BLUE #1 | |

The base formulations may vary by @5% due to drying/dehydration. Sources of active ingredients may include:

| EXEMPLARY ACTIVE INGREDIENT SOURCES |
|---|
| GINGER |

SUPPLIER 1. SOLARAY GINGER Root Extract
Ginger root - 250 mg (5% gingerols)

| EXEMPLARY ACTIVE INGREDIENT SOURCES |
| --- |
| Gingerols - 12.5 mg/5% |
| Other ingredients: Magnesium Sterate, Croscamellose Sodium |
| Park City, UT |
| www.Solaray.com |
| SUPPLIER 2. NATURE'S ANSWER, INC. Ginger Rhizome Extract |
| Ginger Rhizome Exract - 125 mg standardized for 5% gingerols + shogoals) |
| Other ingredients: Vegetable Cellulose, Rice Flour, Di-Calcium Phosphate, Calicium Silicate |
| Hauppauge, NY 11788-3943 |
| http://www.naturesanswer.com/ |
| SUPPLIER 3. SOLGAR GINGER Root Extract |
| Ginger Root Extract - 300 mg (5% ginger phenols) |
| Raw Ginger Powder - 150 mg |
| C-ascorbic acid, beta-carotene, magnesium sterate, monocrystalline cellulose |
| Veronica, NJ SOLGAR GINGER Powder |
| Ginger powder - 500 mg |
| Root Ginger Extract 4:1 - 5 mg |
| L-CITRULLINE |
| SOURCE NATURALS L-Citrulline Free-Form Amino Acid Supplement: |
| L-Citurlline 2 g |
| Other Ingredients: gelatin (capsule), microcrystalline cellulose, colloidal silicon dioxide, and magnesium stearate. |
| Source Naturals, Inc. |
| P.O. Box 2118 |
| Santa Cruz, CA 95062 |
| http://www.sourcenaturals.com/ |
| L-ARGININE |
| THE VITAMIN SHOPPE L-ARGININE |
| L-Arginine - 500 mg |
| Vitamin B6 10 mg |
| Other Ingredients: gelatin, rice flour, magnesium sterate |
| MUIRA PUAMA |
| SUPPLIER 1. SOLARAY Muira Puama Ptychopetalum Olacoides Dietary Supplement: |
| Muira Puama Ptychopetalum Olacoides (root) - 600 mg |
| Other Ingredients: Gelatin Capsule, and Cellulose. |
| Manufactured by Nutraceutical Corp. |
| Park City, UT 84060 |
| http://www.solaray.com |
| SUPPLIER 2. NATURE'S ANSWER Muira Puama Organic Alcohol Extract: |
| Muira Puama Root Extract (1:1) - 2000 mg |
| Other Ingredients: Purified Water, Vegetable Glycerin, 12-15% Certified Organic Alcohol |
| *PAULLINIA CUPANA* (GUARANA) |
| SOURCE NATURALS Guarana Energizer Dietary Supplement: |
| Guarana Seed Extract (22% caffeine) - 900 mg |
| Other Ingredients: Microcrystalline cellulose, dibasic calcium phosphate, stearic acid, modified cellulose gum, and colloidal silicon dioxide. |
| Source Naturals, Inc. |
| P.O. Box 2118 |
| Santa Cruz, CA 95062 |
| http://www.sourcenaturals.com/ |

Since certain preferred compositions of the present inventions comprise compounds found in foods or extracted from foods, they may be referred to as "nutraceuticals." While nutraceutical compositions have traditionally been found in a medicinal format, such as capsules or tablets, an increasing number of foods have been fortified with nutraceuticals. Analogs and/or homologs of ginger constituents that have activity in promoting iNOS sufficient to ameliorate, stop or reverse fibrotic events associated with ED may also be used in combination with L-arginine and/or L-citrulline. The present inventions can therefore be administered in a wide variety of ways and forms matching the lifestyle and dietary preferences of the users, as once or twice a day dietary supplements, mixed into foods or "smoothies," etc. Further, predicate studies of sildenafil have been performed (i.e., Schwartz et al) to show beneficial impact on smooth muscle cells, making it more practical and/or feasible to conduct such studies Clinical Trial An IRB approved clinical trial protocol (see FIGS. 2A-2B) was carried out at a hospital in California. Pursuant to the protocol, patient identity information is not included as well as the location and specific dates that each patient was treated and evaluated. Other information of a confidential nature has been redacted.

A clinical trial was conducted in accordance with the forgoing protocol. Subjects that received the active ingredients composition ingested two capsules of Base formulation 3 (provided supra) twice a day. After one month, data from the first 32 patients showed that the IIEF score was significantly improved in 16, maintained in 15, and lower in one. After two months, 22 patients that had been in the study for two months were evaluated. The erectile function score for the 22 patients included 11 that had significant improvement over their baseline score, 9 maintained their scores and 2 had a lower score. Significance for purposes of improvement was defined as improving one's erectile score by 4 points or more. After three months, patients that stayed in the study maintained improved scores. This is very significant because maintenance of erectile function is important to patients that have been experiencing gradual reduction in function. The muira puama and *paullinia cupana* was not found necessary to achieve these results over a longer duration of administration, so Base Formulation 1 (one capsule twice a day) or Base Formulation 2 (two capsules twice a day) can be used in accordance with the protocol to achieve these results.

Significant medical advancements have resulted from the use of natural products in either their native form, as extracts, or concentrates. For example, acetylsalicyclic acid (or Aspirin) was derived from Willow trees. Likewise, the anticancer drug Taxol was isolated from the Western Yew tree. As a result natural products have been used for treating various diseases for many years. Many natural products have been purported to increase sexual potency, treat sexual problems, or act as aphrodisiacs.

However, there is a great deal of unpredictability due to the complexity of biological systems, variations in plants and their derivatives based on the soil and climate, as well as interactions with other compounds, etc. The present inventor found that by addition of certain natural products, the symptoms of ED appear to be reduced beyond the predicted bioavailability of the compositions of the present inventions; this may be due to growth or restoration of penile CSM, although the invention should not be limited to a particular theory of operation. The clinical trial experience of the present inventor shows that in addition to ginger and L-citrulline or L-arginine, certain natural products used in accordance with the present invention can enhance the effectiveness of and prolong the effects of ED treatment; these include Muira Puama, which is derived from shrubs and trees found in Brazil, and *Paullinia cupana* (also known as guarana), which is derived from a climbing shrub that grows wild in the Amazon regions of Brazil and Uruguay. Muira Puama and *Paullinia cupana* appear to enhance sexual desire. Thus, In an alternative embodiment designed for men showing symptoms of ED, regardless of age, preferred formulations for use at least once a day for the treatment of ED comprise from about 100 mg, preferably at least about 250 mg, to about 2 grams ginger, preferably, about 1 g to about 3 g L-arginine or L-citrulline sufficient to produce the same effect on NO production in vivo as said amount of L-arginine. Preferably, a composition of the present inventions comprises about 250 mg to 2 grams L-arginine or 250 mg to 2 grams L-citrulline (or a mixture of L-arginine and L-citrulline), about 500 mg *Paullinia cupana*, and about 100 mg to about 3 g Muira Puama, preferably about 500 mg to about 1.5 g Muira Puama. The forgoing formulation above may additionally or in place of ginger contain about 20 mg to about 1000 mg 6-gingerol, preferably about 220 mg 6-gingerol, although the present inventor has found it preferable to use ginger or ginger root extract In an embodiment, a preferred composition for the treatment of ED, particularly ARED, comprises about 250 to about 3 grams ginger, about 400 mg L-arginine and/or L-citrulline, about 500 mg *Paullinia cupana*, and about 500 mg to about 1.5 g Muira Puama. The foregoing compositions may also contain CMO and/or FAI, preferably in small amounts from 10 mg to 1 gm and preferably in equal amounts. The formulation above may additionally or in place of ginger contain about 20 mg to about 1000 mg 6-gingerol, preferably about 220 mg 6-gingerol, although the present inventors have found it preferable to use ginger.

A substantial percentage of men at some time in their late twenties and thirties begin to notice that their refractory period begins to increase. This is most likely due to some deterioration beginning to occur in the CSM. Indeed, treatment of men in their 30's who have normal erectile function as measured by the IIEF (International Index of Erectile Function) with the PDE5 inhibitor Viagra increased erectile function as measured by the IIEF and a decrease in the refractory period was possibly due to longer term benefits of the drug, although this could simply be enhanced relaxation of the CSM (Mondiani et al. Int J of Imp Res. 15:225-28, 2003). When men start using these drugs, it is not unusual that after a while, the drugs may begin to lose their effectiveness. When this occurs, it is believed to be due to the continued deterioration of the CSM that occurs with aging rather than tachyphylaxis which is a condition where the tissues lose their reactivity to the drug (Musicki et al. J Urol 174:1493-6, 2004).

Therefore, most men in their late 20's or early 30's who have not had any decrease with their refractory period as well as any man in their 20's and 30's whose refractory period is beginning to increase are those who are candidates to take this composition of the present invention. In addition, any man who is beginning to develop symptoms of ED may also be a candidate for this regimen with the hope that the compositions of the present inventions, taken once daily, will halt or at least slow the progression of the deterioration of the CSM and not further exacerbate preexisting ED treatment and evaluation. Thus, in the aforementioned clinical trial and in a preferred embodiment testing for ED is performed with an IIEF questionnaire. Patients on any treatment regimen for ED may be followed with this IIEF scoring system and this can be performed on an annual basis or more frequently to monitor progression of the ED. With ginger, some patients may experience heartburn, bloating, and stomach upset but these are rare. Ginger in daily doses much higher than the daily doses in compositions of the present invention (ginger at doses greater than 5 g per day) may interact with warfarin a drug that is used to thin the blood (Jellin J. M., et al. (2005). Pharmacist's Letter/Prescriber's Letter of Natural Medicines Comprehensive Database. 7th ed. Stockton, Calif.: Therapeutic Research Faculty). L-citrulline has no known side effects and no known reactions with any other pharmaceutical agents (see for example information available from Global Orphan Pharmaceutical LLC, and at web sites, such as citrullis.com/?page_id=2#SideEffects).

Further studies conducted under the following protocols demonstrate diagnosis, treatment and routine monitoring of erectile function and/or erectile dysfunction. In an embodiment, a treatment for preventing deterioration of one's erectile function, men treated with daily ginger (500 mg) and L-citrulline (1600 mg) in two divided doses would show no deterioration or less deterioration of their erectile function over time. The addition of *paullina cupana* (500 mg/day) and muira puama (500 mg/day) to daily ginger (500 mg) and L-citrulline (1600 mg) would not only prevent deterioration of erectile function as in the first study but would have an excellent chance of improving one's erectile function. Preferably, the formulation does not contain ingredients such as ginseng, oat, oat extract and rosemary. Should the latter be included they are not essential and the formulation can have its desired impact on ED an ARED in their essential absence.

Exemplary formulations include at least ginger and at least one compound selected from the group consisting of L-arginine or L-citrulline. However, while the first two ingredients are ginger and L-arginine, L-arginine can be partially or completely replaced by L-citrulline, so collectively L-citrulline and L-arginine may be referred to as L-arginine since L-citrulline is believe to be converted to L-arginine in vivo and/or have the same effect on NO metabolism. Formulation G-C ("Ginger-L-Citrulline), which comprises ginger and L-citrulline (preferably consists of about 250 mg to about 2 grams ginger and from about 500 mg to about 3 grams L-citrulline. Depending on cost, availability, purity, ease of compounding, shelf life, the ranges of compounds in the formulations and their rheological properties, preferred compositions of the present inventions include ginger and L-arginine (or L-citrulline). In another embodiment, in addition to ginger and L-citrulline or L-arginine, compositions of the present inventions can contain about 50 or 100 mg to about 2 grams Muira puama, about 5 mg to about 500 mg of cortex magnoliae officinalis (CMO), and about 5 mg to about 500 mg fructus aurantil immaturus. (FAI).

DIAGNOSTIC AND PROPHYLAXIS. Substantial barriers exist to conducting routine biopsies on corpus cavernosal ("CC") tissue, e.g., pain, embarrassment, need to avoid erection until the biopsy wound heals, etc. Further, such biopsies must be repeated periodically. Patients must give informed consent before agreeing to the biopsies. Even a patient that has had a radical prostatectomy procedure that included a biopsy of the corporal tissue while under anesthesia may not be willing to have a follow up biopsy, even with assurances of provision of adequate pain relief and the promise that such biopsies can advance the field. Also, a significant problem confronting scientists and Institutional Review Board (IRB) panels is the need to conduct studies of the drug formulations on a double blind basis. So, half of the patients may receive a placebo in place of the drug formulation being tabulated; thus, there is a considerable difficulty in recruiting sufficient patients to provide biopsies, particularly when there is a considerable chance that a placebo will be administered instead of the drug formulation being tested. Further, IRBs may also desire that another study be performed in vitro and/or that animal studies could be used in place of some human studies. In some instances, such study designs may provide substantially the same and/or better data. Financial incentives to trial participants may not draw in a statistically representative group of subjects, and may not reflect a suitable sampling of the relevant population.

However, in a further embodiment of the present inventions, patient histories are collected and evaluated for the occurrence of ED. Patients that have prostate problems, urogenital disorders, and/or cancers in the genital area may be biopsied while under anesthesia for treatment (with prior written informed consent). Some patients may agree to give subsequent biopsy samples, while others will permit a sample to be taken at the time of death. By tracking sufficient family histories, and samples of tissue from patients exhibiting ED symptoms and patients with no ED symptoms, it is possible to identify genes involved in ED. Family histories of ED may also be useful in evaluating ED potential. By identifying patients that are susceptible to ED, even if symptoms have not yet manifested and/or not manifested sufficiently for an individual to require pharmaceutical assistance to achieve full erectile function, compositions of the present invention can be given to candidates while others will receive a placebo. Patients receiving compositions of the present invention that slow or halt ED symptom development, could then qualify for further studies to optimize ingredients, dosages, and period between dosages, etc. Patients that received the placebo and did not improve may be given the other formulation if statistically significant benefits are demonstrated. With sufficient patient data and DNA analysis, it will be possible to identify genetic predisposition to ED symptoms, and prophylaxis treatment can start at the expected age and/or when ED symptoms appear.

While details of certain embodiments of the present inventions are described, they are provided as illustrative examples so as to enable those of ordinary skill in the art to practice the inventions. The details provided are not meant to limit the scope of the present inventions, but to be exemplary. Where certain elements of the present inventions can be partially or fully implemented using known constituents, only those portions of such known constituents that are necessary for an understanding and making of the present invention are described, and detailed descriptions of other constituents or formulating processes are omitted as being to simplify explanation of the invention. Further, the present invention encompasses present and future known equivalents to the compositions and methods referred to herein. The inventions are capable of other embodiments and of being practiced and carried out in various ways, and as such, those skilled in the art will appreciate that the conception upon which this disclosure is based may readily be utilized as a basis for the designing of other methods and compositions for carrying out the several purposes of the present inventions.

The invention claimed is:

1. A pharmaceutical composition for the treatment of erectile dysfunction, consisting essentially of:
   10 mg to 2 g ginger or ginger derivative,
   an effective amount of L-citrulline, L-arginine, or a mixture of L-arginine and L-citrulline,
   an effective amount of muira puama,
   and an effective amount of *paullinia cupana*,
   wherein said composition can be administered in periodic dosages for a sufficient period of time to treat erectile dysfunction or age related erectile dysfunction, and said composition is in an oral dosage form comprising a tablet, capsule, or lozenge.

2. The composition of claim 1, wherein said composition can be administered at least once a day for a period of at least one month to improve erectile function as determined by the International Index of Erectile Function.

3. The composition of claim 1, wherein the ginger derivative is derived from *Zingiber officinale* roscoe or from rhizomes of *Zingiber officinale* roscoe.

4. The composition of claim 1, wherein said composition can be administered periodically for a sufficient period of time to slow, stop or reverse smooth muscle cell deterioration, wherein, when said smooth muscle cell deterioration is associated with a disease comprising at least one of erectile dysfunction and age related erectile dysfunction, said composition can be administered periodically for a sufficient period of time to improve erectile function as determined by the International Index of Erectile Function.

5. The composition of claim 1, wherein said ginger or ginger-derivative is at least one material selected from the group consisting of fresh, partially dried ginger, dried ginger, 6-gingerol.

6. The composition of claim 1, wherein the composition can be administered about once a day for a sufficient period of time to slow, stop or reverse smooth muscle cell deterioration, wherein said smooth muscle deterioration is associated with erectile dysfunction and age related erectile dysfunction.

7. The composition of claim 1, wherein the composition can be administered about once a day for a period of time greater than one month to slow, stop or reverse smooth muscle cell deterioration, wherein said smooth muscle deterioration is associated with erectile dysfunction and age related erectile dysfunction.

8. The composition of claim 1, including 1,600 mg of L-arginine, L-citrulline, or a mixture of L-arginine and L-citrulline.

9. The composition of claim 1, including 500 mg of muira puama.

10. The composition of claim 1, including 500 mg of *paullinia cupana*.

11. A pharmaceutical composition, comprising:
    500 mg of ginger or ginger derivative,
    1,600 mg of L-citrulline, L-arginine, or a mixture of L-arginine and L-citrulline,
    500 mg of muira puama,
    and 500 mg of *paullinia cupana*,
    wherein said composition can be administered in periodic dosages for a sufficient period of time to treat erectile dysfunction or age related erectile dysfunction, and said composition is in an oral dosage form comprising a tablet, capsule, or lozenge.

12. The composition of claim 11, wherein the composition can be administered at least once a day for a period of at least one month to improve erectile function as determined by the International Index of Erectile Function.

13. The composition of claim 11, wherein the ginger derivative is derived from *Zingiber officinale* roscoe or from rhizomes of *Zingiber officinale* roscoe.

14. The composition of claim 11, wherein the composition can be administered periodically for a sufficient period of time to slow, stop or reverse smooth muscle cell deterioration.

15. The composition of claim 11, wherein the ginger or ginger derivative is at least one material selected from the group consisting of fresh, partially dried ginger, dried ginger, 6-gingerol.

16. The composition of claim 11, wherein the composition can be administered at least once a day for a sufficient period of time to slow, stop or reverse smooth muscle cell deterioration, wherein smooth muscle deterioration is associated with erectile dysfunction and age related erectile dysfunction.

17. The composition of claim 11, wherein the composition can be administered about once a day for a period of time greater than one month to slow, stop or reverse smooth muscle cell deterioration, wherein smooth muscle deterioration is associated with erectile dysfunction and age related erectile dysfunction.

* * * * *